US006580942B1

(12) United States Patent
Willshire

(10) Patent No.: US 6,580,942 B1
(45) Date of Patent: Jun. 17, 2003

(54) HEART ACTIVITY DETECTION APPARATUS

(75) Inventor: Richard John Willshire, Chichester (GB)

(73) Assignee: Healthcare Technology Limited (GB)

( * ) Notice: Subject to any disclaimer, the term of this patent is extended or adjusted under 35 U.S.C. 154(b) by 0 days.

(21) Appl. No.: 09/542,358

(22) Filed: Apr. 4, 2000

(30) Foreign Application Priority Data

Apr. 7, 1999 (GB) ............................................... 9907789

(51) Int. Cl.[7] ................................................. A61B 5/04
(52) U.S. Cl. ...................................... 600/509; 600/523
(58) Field of Search ................................. 600/509, 523

(56) References Cited

U.S. PATENT DOCUMENTS

| 3,830,227 A | | 8/1974 | Green |
| 4,004,577 A | * | 1/1977 | Sarnoff ........................ 128/904 |
| 4,270,547 A | | 6/1981 | Steffen et al. |
| 4,350,164 A | | 9/1982 | Allain, Jr. |
| 4,825,874 A | | 5/1989 | Uhlemann |
| 5,016,636 A | * | 5/1991 | Kulakowski ................ 600/390 |

FOREIGN PATENT DOCUMENTS

| EP | 0653182 | 5/1995 |
| EP | 0666055 | 8/1995 |
| GB | 2168727 | 1/1985 |
| GB | 2168817 | 6/1986 |

OTHER PUBLICATIONS

Search Report Jul. 6, 1999.

* cited by examiner

*Primary Examiner*—Mark Bockelman
(74) *Attorney, Agent, or Firm*—Ira S. Dorman

(57) ABSTRACT

Activity of an animal heart is detected with an apparatus comprising a housing (20) within which is contained electronic circuitry (32, 34, 36, 38, 40), a power supply (46) for the circuitry, and an indicator (42, 44) connected to the circuitry which can be operated by the circuitry to generate an alerting signal detectable by a user. In addition there is a pair of sensors (28) electrically connected to convey to the circuitry electrical signals detected by the sensors. The circuitry is operative to analyse signals received from the sensors, and upon determination that such signals are electrocardiographic signals derived from a heart beat to cause the indicator (42, 44) to operate so as to generate an alerting signal.

17 Claims, 2 Drawing Sheets

HEART ACTIVITY DETECTION APPARATUS

The present invention relates to apparatus for detecting activity of an animal heart. The apparatus has particular, but not exclusive, application in detecting activity of a human heart.

BACKGROUND TO THE INVENTION

In an emergency in which a person has been rendered unconscious, either through accident or illness, one of the most crucial pieces of information required by a carer is whether or not the afflicted person's heart is beating. If the person's heart has stopped, suitable resuscitation measures must be taken as a matter of extreme urgency if brain damage is to be avoided. However, such resuscitation measures can be dangerous, and it is of importance that they are not applied to a person whose heart is still beating.

The traditional approach has been for a carer to feel for a pulse beat. To do this, the carer attempts to find a pressure point on the person's body where arteries are close to the surface of the skin. A finger pressed against the arteries can then feel pressure pulses caused by blood being pumped by the heart.

Skill is required to perform this procedure reliably. The precise position of pressure points on a body varies from individual to individual. One locates a pressure point by probing with a finger until a maximum pulsation due to the heart pumping is felt. If the heart is beating faintly, a failure to locate precisely the pressure point could give the false impression of the heart having stopped. The clamour and confusion of an emergency situation makes this procedure all the more difficult. A carer is likely to be under stress, and will find it difficult to search diligently for an active pressure point, because his or her hands are shaking, because there is so much commotion at the site, or because his or her own heart beat pulsations are so strong that they mask those sensed on the patient's body.

Moreover, the carer cannot undertake continual monitoring of the person while attending to other tasks. This gives rise to a risk that a deterioration in the person's condition might go un-noticed.

OBJECT OF THE INVENTION

An object of the invention is to provide apparatus which can accurately and reliably monitor a person's heart activity in a form which can readily be used by a comparatively unskilled operator.

SUMMARY OF THE INVENTION

According to the present invention there is provided an apparatus for detecting heart activity of an animal heart comprising a housing within which is contained electronic circuitry, a power supply for the circuitry, and an indicator connected to the circuitry operable by the circuitry to generate an alerting signal detectable by a user, the apparatus further comprising a pair of sensors electrically connected to convey to the circuitry electrical signals detected by the sensors, the circuitry being operative to analyse signals received from the sensors and, upon determination that such signals are electrocardiographic signals derived from a heart beat, to cause the indicator to operate so as to generate an alerting signal.

Thus, while signals are being generated by the apparatus, the carer is reassured that the afflicted person's heart remains active. If the signals should cease, or not issue upon application of the sensors to a person, this indicates that the person's heart may have stopped and that immediate remedial action is required.

The indicator may issue visual signals (for example, it may be a light-emitting diode) or audible signals (it may be a sounder). Both of the aforementioned indicators may be provided, optionally in combination with additional indicators of any suitable type.

The housing may be of a type which permanently encapsulates components contained within it, and which is not intended to be opened subsequent to manufacture. This minimises the risk that the working parts of the apparatus will be subject to tampering.

The sensors may be in the form of electrodes and are preferably carried on wings extending from the housing. The wings are normally dimensioned to ensure that the electrodes are properly positioned when the apparatus is placed on a person's chest. The wings are preferably not separable (other than by their destruction) from the housing. Most preferably, the wings are made from a flexible material so that they can be folded around or adjacent the housing for storage. The wings may be made from a conductive material, such as a conductive rubber, or they may have conductors embedded within them. Adhesive may be provided adjacent to the electrodes to enable them to be retained in contact with a person's skin.

The circuitry preferably includes a switch, operative automatically to energise the circuitry upon detection of completion of a circuit between the electrodes. This causes the apparatus to start working automatically upon application on a person.

The circuitry preferably includes a rectification stage to ensure that the apparatus will operate irrespective of which electrode is placed upon one or other side of a person's chest.

For a better understanding of the present invention and to show more clearly how it may be carried into effect reference will now be made, by way of example, to the accompanying drawings in which:

DESCRIPTION OF PREFERRED EMBODIMENT

Apparatus embodying the invention operates by detecting electrical signals generated on a person's chest by their beating heart. These signals are referred to as electrocardiographic signals, and the usual abbreviation therefor, ECG signals, will be used in this specification.

Figure 1:
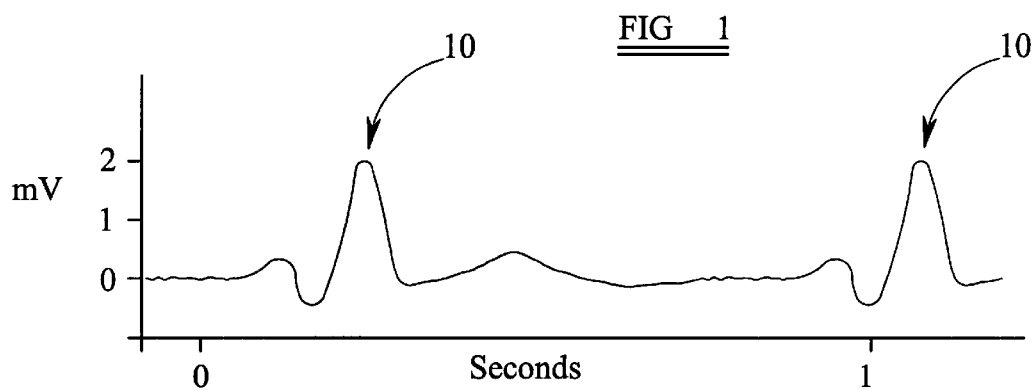
FIG. 1 is a graph of the potential of a typical electrical signal which appears across a person's chest generated by a beating heart.

The trace shown in FIG. 1 is typical of that which might be picked up from a human chest by electrodes placed on it, spaced apart horizontally just below the person's nipples. The trace of FIG. 1 shows a typical cycle of voltages that might be detected in a period covering a little more than one complete beat of the heart. The repeating cycle of voltages is quite complex in nature. The most notable event in each cycle is a voltage peak (shown at 10), known as the "R-wave", in which the electrode on the person's left side goes positive with respect to the electrode on the user's right side by approximately 2 mV. The apparatus of the present embodiment searches for the presence of an R-wave as an indication of heart activity.

Figure 2:
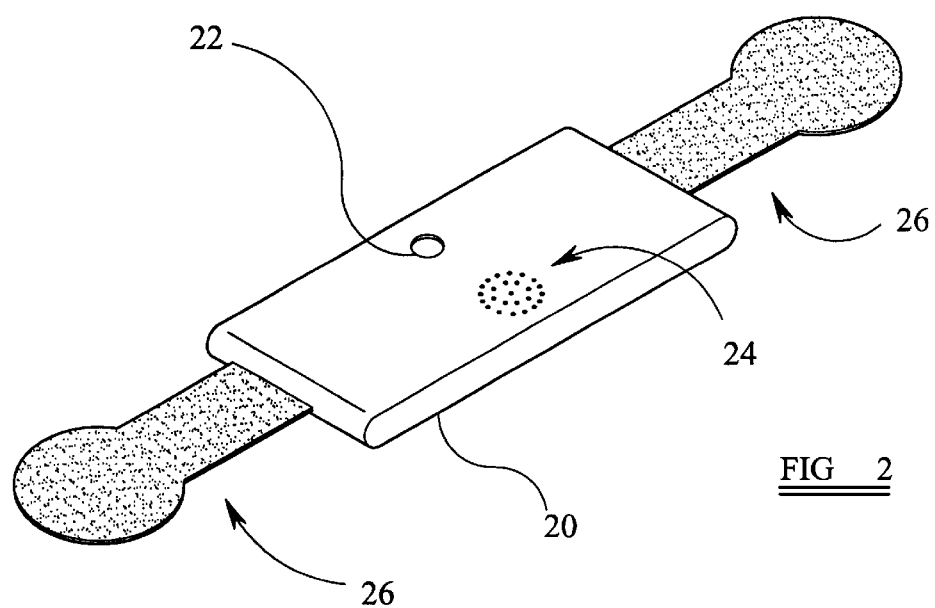
FIG. 2 shows apparatus embodying the invention.
Figure 3:
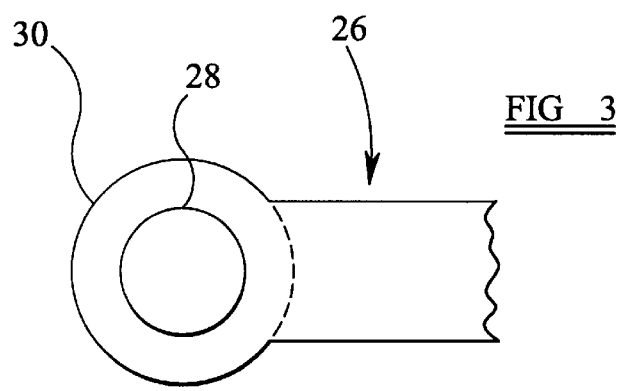
FIGS. 3 and 4 show in more detail an electrode being part of the embodiment shown in FIG. 2.
Figure 4:
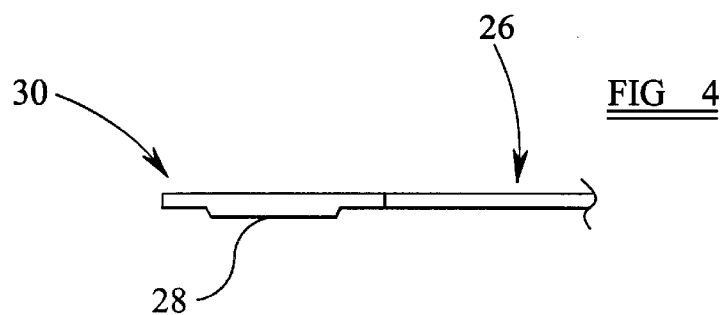
Figure 5:
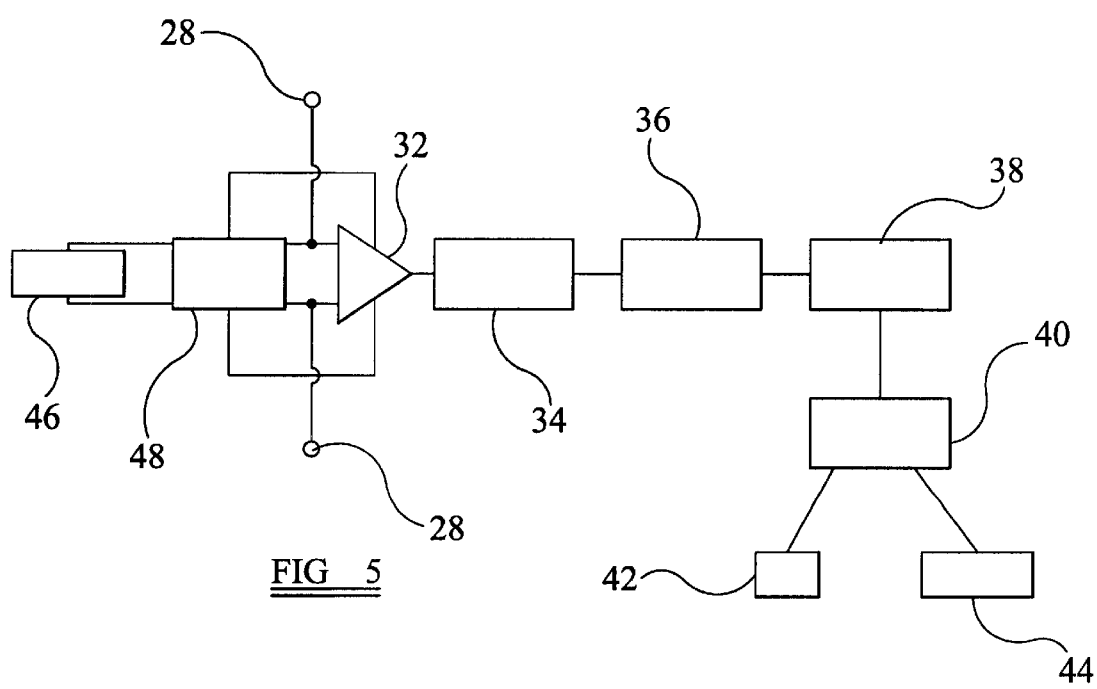
FIG. 5 is a block diagram of electronic circuitry contained within the apparatus of FIG. 2.

External features of apparatus for detection of heart activity being an embodiment of the invention are shown in FIGS. 2, 3 and 4.

The apparatus includes a housing 20 of robust material. The housing is rectangular in plan, and as thin as possible to contain the circuitry within. The housing 10 contains operational electronic circuitry which will be described below. A viewing aperture 22 is formed though an upper surface of the housing 10 through which a light-emitting diode located within the housing 20 can be seen. A group of small holes 24 is formed next to the viewing aperture 22 through which sound from a sounder within the housing 20 can escape.

Two wings 26 project in opposite directions from the housing 20. Each wing 26 includes a flexible elongate strip which extends from the housing 20. Remote from the housing, each wing has a bulbous end portion 30. Each bulbous end portion carries a conductive electrode 28 on a lower surface. The strip, the end portion 30 and the electrode 28 can conveniently be formed in one piece from an electrically conductive, flexible rubber material.

As shown in FIGS. 3 and 4, on the lower surface of the bulbous end portion, the electrode 28 is surrounded by an annular region, the electrode 28 protruding a small distance from the annular region. During manufacture, the annular region is coated with an adhesive composition, and a protective sheet is applied to cover the adhesive and the electrode 28.

Immediately before use of the apparatus, a protective sheet is removed from each wing 26. The housing 20 is then placed upon the afflicted person's chest. The electrodes 28 are pressed into contact with the person's skin, and pressure is applied to the adhesive to retain the electrodes 28 in place.

Any ECG signals appearing between the electrodes 28 cause a signal to be conducted through each of the wings 26 to the circuitry within the housing 20.

The construction and operation of the electronic circuitry will now be described.

An electrical connection is made from each of the wings 26 to a respective input of an amplifier 32. The output of the amplifier 32 is fed to a full-wave rectifier 34. If the signal were not rectified, the apparatus would only work when placed on the subject in one left-to-right orientation.

The rectified signal is fed to a filter circuit 36 which serves to extract the R-wave from the rest of the ECG signal. The filter circuit 36 passes signal components in a frequency band which contains frequencies which typically make up the R-wave. The filter circuit 36 typically includes a band-pass filter with a centre frequency of about 11 Hz. The filter circuit 36 serves also to reject false signals for example, those generated by muscles other than heart muscles and by movement of the electrodes 28 on the person's chest.

The output signal from the filter circuit 36 is passed to a discriminator 38 which generates an output if the filtered signal rises above a preset threshold level. If the discriminator is triggered, it generates an output signal to fire a monostable 40. The output from this monostable 40, typically a pulse of about 20 ms duration, causes a light emitting diode 42 to illuminate briefly, and a sounder 44 generate an audible tone.

The occurrence of regular flashes in the light-emitting diode 42 (visible through the viewing aperture 22) and audible tones indicates to a user that the person's heart is beating. This observation can be made from a distance by a carer while attending to other matters. Moreover, this is a less ambiguous indication of heart activity in a time of crisis than is the traditional technique.

Power for the circuitry is derived from a battery 46. An important feature of the battery selected is that it has a long shelf life (preferably up to 10 years) because in many cases, the apparatus will not be used for many years after its manufacture.

The battery 46 is connected to the electronic circuitry by an electronic switch 48. The switch 48 has sensing inputs electrically connected to the wings 26. The sensing inputs monitor conductivity between the contacts 20, and turn on the switch when the conductivity exceeds a threshold, as would happen when the electrodes 28 make contact with a person's skin. The conductivity sensing circuit within the switch 48 consumes a very small current: only a small fraction of one microamp. This current is sufficiently small to discharge the battery at a slow enough rate to confer a long storage life upon the apparatus. When the apparatus is in use, the battery will be discharged significantly, so the apparatus can be considered to be capable of being used only a very small number of times, and maybe once only.

I claim:

1. An apparatus for detecting heart activity of an animal heart comprising a housing within which is contained electronic circuitry, a power supply for the circuitry, and an indicator connected to the circuitry and operable by the circuitry to generate an alerting signal detectable by a user, the apparatus further comprising a pair of elongate strips extending in opposite directions from the housing and provided, in the region of a free end of each thereof, with a sensor, the elongate strips being dimensioned such that, when the housing is placed on a person's chest, the sensors are positioned at spaced locations on the person's chest, the sensors being electrically connected to convey to the circuitry electrical signals detected by the sensors, the circuitry being operative to analyse signals received from the sensors and, upon determination that such signals are electrocardiographic signals received from the sensors and, upon determination that such signals are electrocardiographic signals derived from a heart beat, to cause the indicator to operate so as to generate an alerting signal.

2. An apparatus according to claim 1, wherein the indicator issues visual signals.

3. An apparatus according to claim 2, wherein the indicator comprises a light-emitting diode.

4. An apparatus according to claim 1, wherein the indicator issues audible signals.

5. An apparatus according to claim 4, wherein the indicator comprises a sounder.

6. An apparatus according to claim 1, wherein the housing permanently encapsulates components contained within it, and is not intended to be opened subsequent to manufacture.

7. An apparatus according to claim 1, wherein the sensors are in the form of electrodes.

8. An apparatus according to claim 1, wherein the sensors are on wings extending from the housing.

9. An apparatus according to claim 8, wherein the wings are dimensioned to ensure that the sensors are properly positioned when the apparatus is placed on a person's chest.

10. An apparatus according to claim 8, wherein the wings are not separable from the housing.

11. An apparatus according to claim 1, wherein the elongate strips are made from a flexible material so that they can be folded around or adjacent the housing for storage.

12. An apparatus according to claim 1, wherein the elongate strips are made from a conductive material.

13. An apparatus according to claim 12, wherein the elongate strips are made from a conductive rubber.

14. An apparatus according to claim 1, wherein the elongate strips have conductors embedded within them.

15. An apparatus according to claim 1, wherein adhesive is provided adjacent to the sensors to enable them to be retained in contact with a person's skin.

16. An apparatus according to claim 1, wherein the circuitry includes a switch which is operative automatically to energise the circuitry upon detection of completion of a circuit between the sensors.

17. An apparatus according to claim 1, wherein the circuitry includes a rectification stage to ensure that the apparatus is operable irrespective of which sensor is placed upon one or other side of a person's chest.

* * * * *